(12) United States Patent
Ringo (10) Patent No.: US 10,537,665 B2
(45) Date of Patent: Jan. 21, 2020

(54) PERFORATED TISSUE MATRIX

(71) Applicant: LifeCell Corporation, Branchburg, NJ (US)

(72) Inventor: Alexander Ringo, Somerset, NJ (US)

(73) Assignee: LifeCell Corporation, Madison, NJ (US)

( * ) Notice: Subject to any disclaimer, the term of this patent is extended or adjusted under 35 U.S.C. 154(b) by 245 days.

(21) Appl. No.: 15/260,416

(22) Filed: Sep. 9, 2016

(65) Prior Publication Data

US 2017/0072110 A1    Mar. 16, 2017

Related U.S. Application Data

(60) Provisional application No. 62/217,353, filed on Sep. 11, 2015.

(51) Int. Cl.
| | |
|---|---|
| *A61L 27/60* | (2006.01) |
| *A61K 35/36* | (2015.01) |
| *A61F 2/10* | (2006.01) |
| *A61L 27/50* | (2006.01) |
| *A61L 27/36* | (2006.01) |
| *A61F 2/00* | (2006.01) |

(52) U.S. Cl.
CPC ............ *A61L 27/50* (2013.01); *A61F 2/0063* (2013.01); *A61K 35/36* (2013.01); *A61L 27/362* (2013.01); *A61L 27/3633* (2013.01); *A61L 27/60* (2013.01); *A61L 2430/34* (2013.01); *A61L 2430/40* (2013.01)

(58) Field of Classification Search
CPC ............ A61F 2/0063; A61F 2002/0081; A61F 2002/0068; A61L 27/60; A61L 27/362; A61L 27/3633; A61K 35/35; A61K 35/36
See application file for complete search history.

(56) References Cited

U.S. PATENT DOCUMENTS

| | | | |
|---|---|---|---|
| 3,446,213 A | 5/1969 | Goldman | |
| 3,902,198 A | 9/1975 | Cooper | |
| 7,723,108 B2 * | 5/2010 | Truncale | ................ A01N 1/02 |
| | | | 435/378 |
| 8,323,352 B2 | 12/2012 | Friedman et al. | |
| 8,323,701 B2 | 12/2012 | Daniel et al. | |
| 8,986,377 B2 | 3/2015 | Richter et al. | |
| 9,114,003 B2 | 8/2015 | Kalus | |
| 9,351,819 B2 | 5/2016 | Harper | |

(Continued)

FOREIGN PATENT DOCUMENTS

| | | |
|---|---|---|
| WO | 97/06837 A1 | 2/1997 |
| WO | 2007/004214 A2 | 1/2007 |

OTHER PUBLICATIONS

Ge et al.; Comparison of histological structure and biocompatibility between human acellular dermal matrix (ADM) and porcine ADM; Burns; 35 (2009);p. 46-50.*

(Continued)

*Primary Examiner* — Dinah Baria
(74) *Attorney, Agent, or Firm* — McCarter & English, LLP; Matthew R. Van Eman (57) ABSTRACT

The present disclosure relates to tissue matrix products. The products can includes tissue matrices that have holes or perforations located at certain positions to improve certain in vivo functions without substantial loss of strength or other important properties.

18 Claims, 7 Drawing Sheets

(56) References Cited

U.S. PATENT DOCUMENTS

| | | |
|---|---|---|
| 2004/0034374 A1 | 2/2004 | Zatzsch et al. |
| 2007/0088434 A1 | 4/2007 | Frank |
| 2009/0082864 A1 | 3/2009 | Chen et al. |
| 2011/0166673 A1 | 7/2011 | Patel et al. |
| 2011/0208320 A1 | 8/2011 | Stevenson et al. |
| 2012/0158134 A1 | 6/2012 | Codori-Hurff et al. |
| 2012/0283826 A1 | 11/2012 | Moses et al. |
| 2014/0100655 A1 | 4/2014 | Diaz et al. |
| 2015/0157451 A1 | 6/2015 | Bowley et al. |

OTHER PUBLICATIONS

Adelman, David M., Jesse C. Selber, and Charles E. Butler. "Bovine versus porcine acellular dermal matrix: a comparison of mechanical properties." Plastic and Reconstructive Surgery Global Open 2.5 (May 2014).

Cavallo, J. A., et al. "Remodeling characteristics and biomechanical properties of a crosslinked versus a non-crosslinked porcine dermis scaffolds in a porcine model of ventral hernia repair." Hernia 19.2 (Mar. 2013): 207-218.

International Search Report and the Written Opinion for PCT/US2016/050865 dated Nov. 21, 2016, pp. 1-14.

Tsuda, Shawn. "Laparoscopic repair of complicated umbilical hernia with Strattice Laparoscopic™ reconstructive tissue matrix." International journal of surgery case reports 5.12 (Nov. 2014): 1167-1169.

\* cited by examiner

PERFORATED TISSUE MATRIX

This application claims priority to U.S. Provisional Patent Application 62/217,353, filed Sep. 11, 2015 and incorporated herein by reference in its entirety.

The present disclosure relates generally to acellular tissue matrix products, including tissue matrix products having perforations or holes at certain locations.

Surgeons currently use acellular tissue matrix products such as ALLODERM® and STRATTICE™, both dermal acellular matrices produced by LIFECELL® CORPORATION (Branchburg, N.J.), for treatment of a variety of different structural defects. For example, such products can be useful in abdominal wall repair (e.g., complex hernia repair), breast reconstruction, orthopedic surgery, and neurosurgical applications.

Such tissue matrix products are often provided as flexible sheets of material that can replace, augment, or alter existing tissues. For some applications, however, it may be desirable to include holes or openings in the sheets, for example, to permit more rapid fluid flow across the sheets or to provide sites for securing surgical anchors such as sutures, clips, or staples.

Accordingly, the present application provides tissue matrix products having preformed holes or perforations. The holes or perforations are provided in a configuration that provides the desired functionality without sacrificing other properties such as strength and suture retention.

According to certain embodiments, a tissue matrix product is provided. The product can include a flexible sheet comprising a tissue matrix, wherein the flexible sheet includes a group of holes passing through the tissue matrix, wherein the holes are formed in a pattern comprised of a repeating motif of five holes.

In other embodiments, a tissue matrix comprising a flexible sheet comprising a tissue matrix is provided. The flexible sheet includes a group of between 10 and 80 holes passing through the tissue matrix, wherein the flexible sheet comprises a rectangular shape having a width between 10 cm and 30 cm and a length between 10 cm and 30 cm, and the holes have a maximum dimension between about 1.5 mm and 2.5 mm, and wherein the holes are arranged in a pattern such that a uniaxial tensile strength measured in any direction along the sheet is at least 60% of the uniaxial tensile strength of the sheet without the group of holes.

In other embodiments, a tissue matrix including a flexible sheet comprising a tissue matrix is provided. The flexible sheet includes a group of between 10 and 80 holes passing through the tissue matrix, wherein the flexible sheet comprises a rectangular shape having a width between 10 cm and 30 cm and a length between 10 cm and 30 cm, and the holes have a maximum dimension between about 1.5 mm and 2.5 mm, and wherein the holes are arranged in a pattern such that a straight line drawn obliquely across a top or bottom surface of the tissue matrix can pass through no more than three of the holes.

Also provided are methods of treatment including the disclosed products.

BRIEF DESCRIPTION OF THE DRAWINGS

Reference will now be made to exemplary embodiments, examples of which are illustrated in the accompanying drawings. Wherever possible, the same reference numbers will be used throughout the drawings to refer to the same or like parts. The drawings are not necessarily to scale.

DESCRIPTION OF EXEMPLARY EMBODIMENTS

Reference will now be made in detail to various embodiments of the disclosed devices and methods, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure relates generally to devices for surgical procedures and systems and methods relating to such devices. The devices can be used for tissue augmentation, repair or regeneration of damaged tissue, and/or correction of tissue defects. As such, the devices and methods discussed herein can be suitable for a wide range of surgical applications, such as, for example, abdominal wall repair, prophylactic treatment of post-operative complications (e.g., to prevent hernia, dehiscence, or other post-operative abdominal complications), hernia treatment (e.g., any abdominal or visceral hernia, such as a hiatal hernia, inguinal hernia, parastomal hernia, or midline abdominal hernia). The devices disclosed herein can also be used to treat other tissue sites, including, for example, breasts, connective tissue (tendons, ligaments, or fascia), and to assist in any structural defect correction or prevention.

The devices and associated methods discussed herein can include a flexible sheet of biologic material, such as an acellular tissue matrix. Such tissue matrix materials are used for a variety of surgical applications and have become an important tool for treating or preventing many problems associated with trauma, post-operative complications, and/or structural defects due to aging, disease, congenital or acquired defects, or iatrogenic problems.

For some surgical procedures, it may be desirable to include holes or openings in the tissue matrix. For example, in some cases, it is desirable to place a drainage tube near a surgical site to allow drainage of fluids, e.g., to prevent formation of seromas or other fluid accumulations. Drainage of fluid from opposite sides of implantable tissue matrices, however, can be improved by providing holes or fluid passages through the matrices so that a drainage device located on one side will collect fluids from both sides of the device.

In addition, properly designed holes or openings can be useful for securing the tissue matrices. For example, some tissue matrix materials are designed to be strong and potentially relatively thick. Accordingly, fixation of such devices to surrounding tissues using conventional means such as sutures, staples, or clips, can sometimes be challenging and/or time consuming. Therefore, tissue matrices with preformed holes that can be used for fixation using sutures or other means are desirable.

On the other hand, holes or openings in tissue matrices should be configured to prevent unacceptable changes in other materials properties. For example, a group of holes in a flexible sheet of tissue matrix must be sized, shaped, and positioned such that the tissue matrix does not experience an unacceptable degradation in important mechanical properties such as tensile strength, elasticity, burst strength, and/or suture retention strength. Accordingly, the present application provides improved tissue matrix products that include a group of holes or perforations that are specially configured to provide the aforementioned advantages without causing unacceptable alterations in other material properties. As used herein, "holes" and "perforations" are used interchangeably and will generally refer to any opening that passes through a flexible sheet of material from one side to the other.

According to certain embodiments, the present application provides tissue products for use in surgical procedures. The tissue products can include a flexible sheet 10 (FIGS. 2A-C) comprising a tissue matrix, wherein the flexible sheet includes a group of holes 20 passing through the tissue matrix 10. The holes 20 can be placed on the sheet in a specifically designed pattern. In one embodiment, the holes are placed using a repeating motif 30 (FIG. 2B).

As used herein "motif" will be understood to refer to any repeatable pattern of holes. Further, the motif need not be repeated exactly, but can be varied (e.g., by changing dimension of holes or spacing of holes), so long as one or all of the goals discussed herein are met.

According to other embodiments, the present application provides tissue products including a flexible sheet 10 comprising a tissue matrix and a group of holes 20. The holes 20 are sized and positioned on the flexible sheet of tissue matrix 10 to maintain a desired tensile strength of the sheet, as compared to a sheet without the group of holes 20.

According to other embodiments, the present application provides tissue products including a flexible sheet 10 comprising a tissue matrix and a group of holes 20. The group of holes are positioned such that the number of holes that are aligned along an oblique axis of the sheet is minimized or kept below a certain level. For example, in one embodiment, the holes 20 are arranged in a pattern such that a straight line 80, 81 (FIG. 2C) drawn obliquely across a top or bottom surface of the tissue matrix can pass through no more than three of the holes 20.

Figure 1:
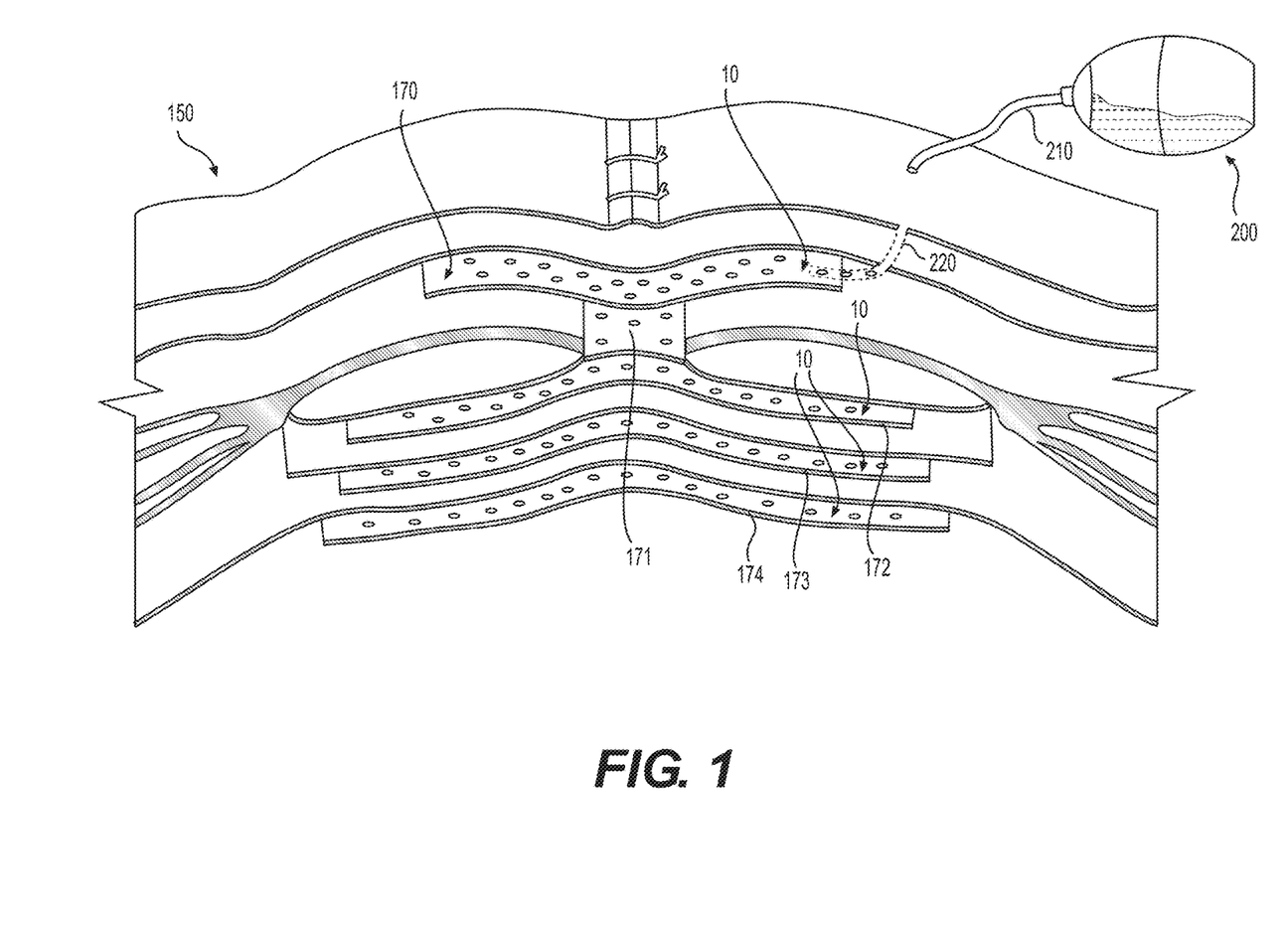
FIG. 1 illustrates methods of treatment of an abdominal wall using tissue matrix products of the present application.

The devices disclosed herein can be used for treating a variety of different anatomic sites. For example, FIG. 1 illustrates methods of treatment of an abdominal wall using tissue matrix products 10 of the present application. The methods of treatment are described in more detail below, but in general, the device 10 can be used to treat portions of the abdominal wall 150, while using the group of holes 20 to allow fluid flow through the devices or to provide a site for fixation using sutures or other fixation means. Furthermore, as discussed below, the devices 10 can be implanted at a variety of different locations to support various anatomic structures and/or treat a variety of different conditions.

Figure 2A:
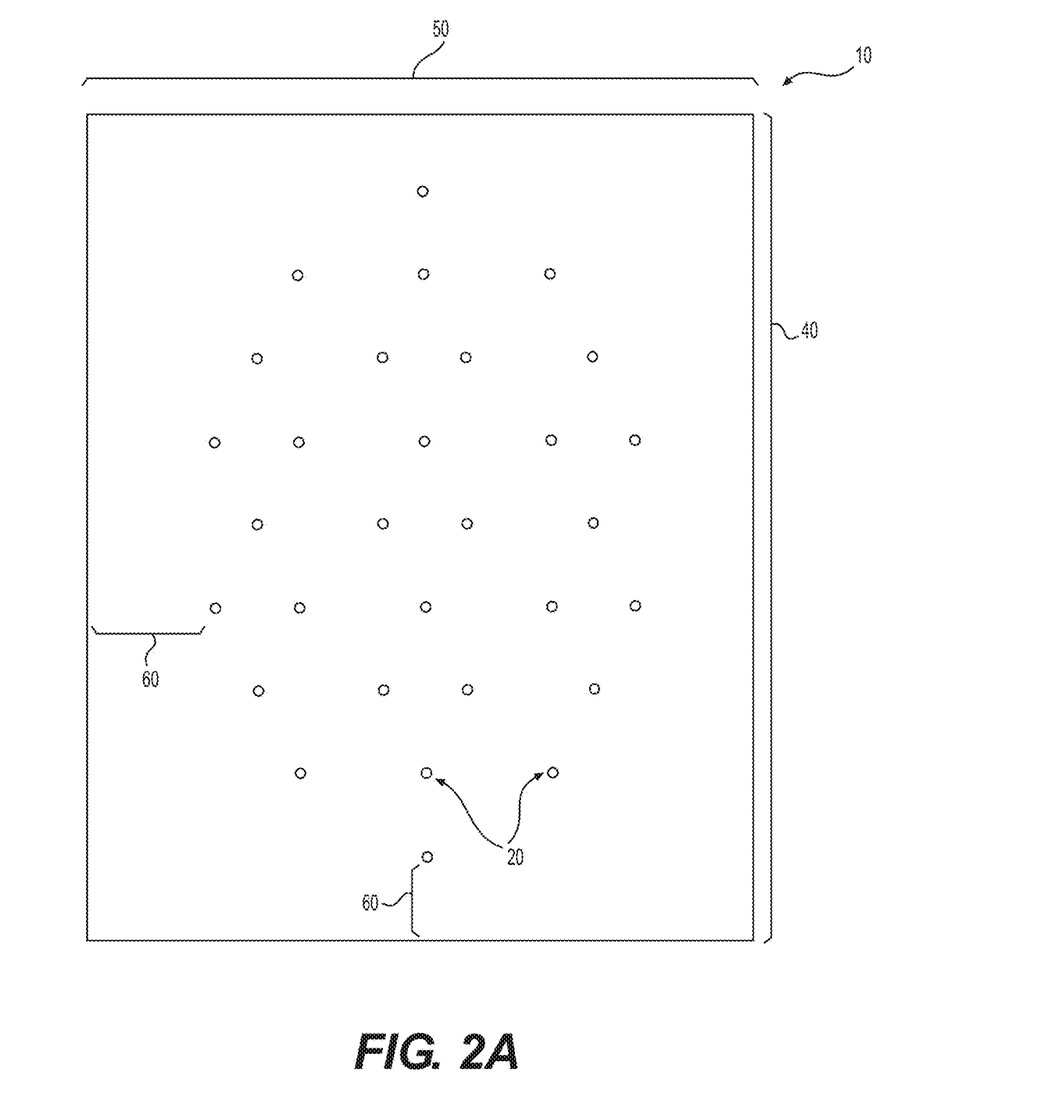
FIG. 2A illustrates a tissue matrix product including holes or perforations, according to certain embodiments.
Figure 2B:
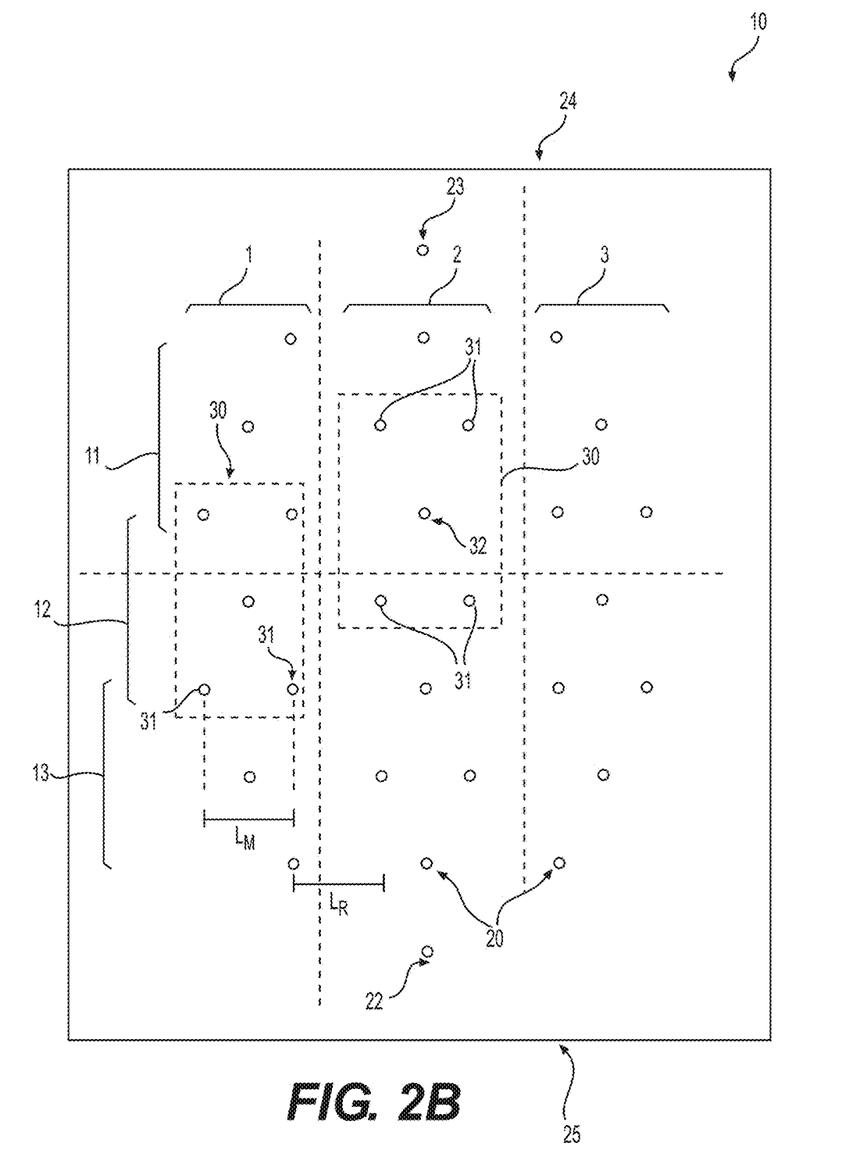
FIG. 2B illustrates the tissue matrix product of FIG. 2A with various features highlighted, according to certain embodiments.
Figure 2C:
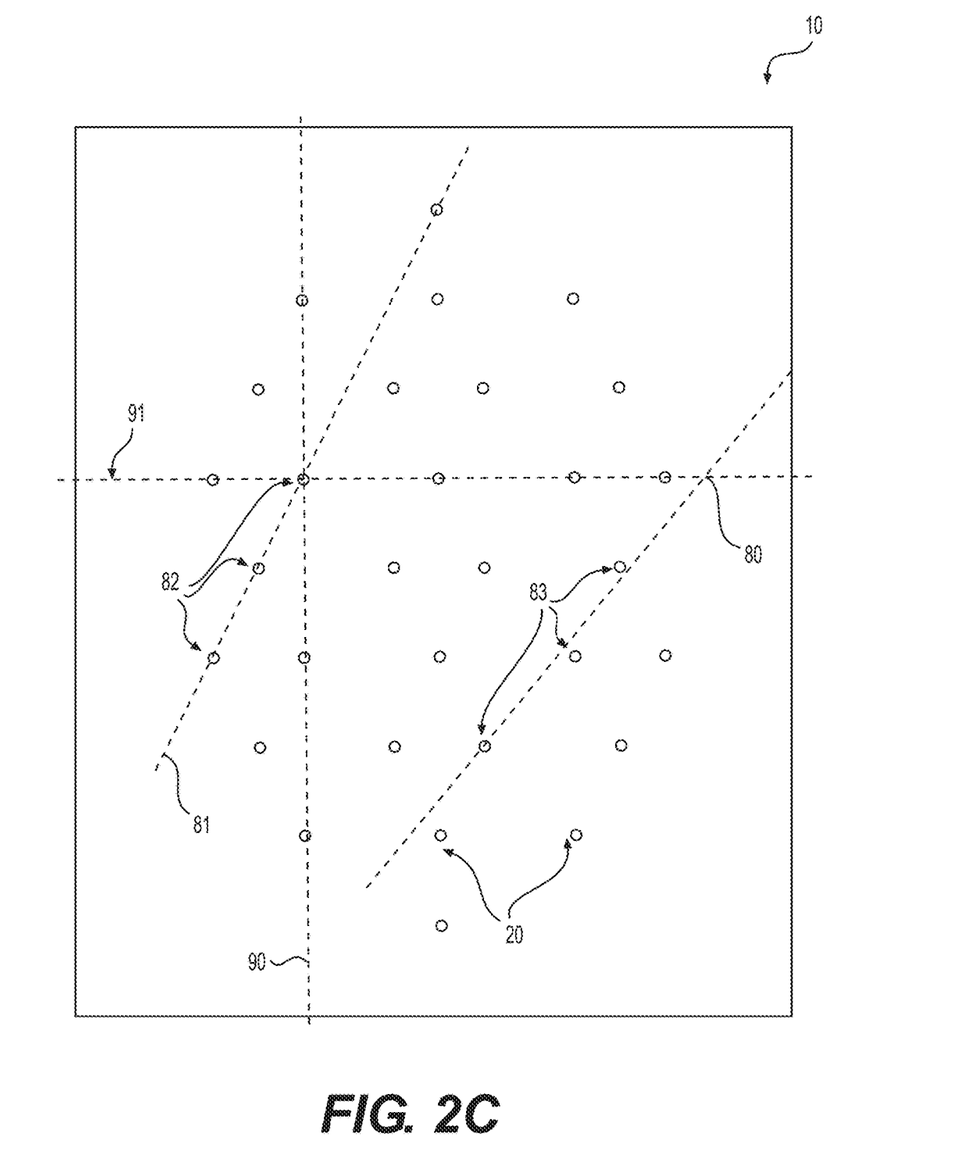
FIG. 2C illustrates the tissue matrix product of FIG. 2A with various features highlighted, according to certain embodiments.

FIGS. 2A-2C illustrate an exemplary tissue matrix product 10 including holes or perforations, according to certain embodiments. The products 10 illustrated in each of FIGS. 2A-2C are identical but include different reference numerals and markings to facilitate discussion of various features of the product 10.

The tissue matrix product 10 is illustrated as a two-dimensional view of a flexible sheet of material. Accordingly, it should be appreciated that the flexible sheet will have a length 40 and width 50, and a thickness (not shown). The length 40, width 50, and thickness can be selected based on the desired surgical indication, e.g., to provide a sufficient surface area (measured in terms of the length 40 and width 50) and structural stability (e.g., based on strength, tensile properties, suture retention, burst strength, etc.). For dermal tissue matrix materials, the thickness can vary, but may be between, for example, 0.75 mm to 4 mm, 0.75 mm to 1.25 mm, or 1.05 mm to 1.55 mm.

The tissue matrices used to produce the products 10 described herein can include a variety of different materials. For example, an acellular tissue matrix or other tissue product can be selected to allow tissue ingrowth and remodeling to assist in regeneration of tissue normally found at the site where the matrix is implanted. For example, an acellular tissue matrix, when implanted on or into subdermal tissue, fascia, mammary tissue, or other tissue, may be selected to allow regeneration of the tissue without excessive fibrosis or scar formation. In certain embodiments, the devices can be formed from ALLODERM® or STRATTICE™ (LIFE-CELL® CORPORATION, BRANCHBURG, N.J.) which are human and porcine acellular dermal matrices, respectively. Alternatively, other suitable acellular tissue matrices can be used. For example, a number of biological scaffold materials as described by Badylak et al., or any other similar materials, can be used. Badylak et al., "Extracellular Matrix as a Biological Scaffold Material: Structure and Function," *Acta Biomaterialia* (2008), doi:10.1016/j.actbio.2008.09.013. The devices described herein can be produced from a variety of different human or animal tissues including human, porcine, ovine, bovine, or other animals tissues.

As stated above, the products 10 can include a group of holes 20 that can be sized and positioned to provide a number of desired properties. As illustrated in FIG. 2A, the product 10 includes a total of thirty holes, but a range in the number of holes can be used, as discussed further below. Further, as shown in FIG. 2A, the holes 20 can be positioned such that a perimeter region 60 is formed in which no holes 20 are present. The perimeter region 60 can be sized to allow an area for passage of sutures or other connection devices and/or to provide a non-perforated section for fixation to tissue such as fascia. Suitable sizes may include 1.5-3 cm, 2-2.5 cm, about 2 cm, 1.5-2.5 cm, or values in between. Larger or smaller perimeter regions 60 can be used.

To provide the desired functional properties, the group of holes 20 can be positioned in specialized patterns. For example, in one embodiment, the group of holes 20 are positioned using a repeating motif 30. The motif 30 can be selected to allow formation of a desired number of holes 20 without unacceptable changes in certain material properties such as strength or elasticity.

Figure 3:
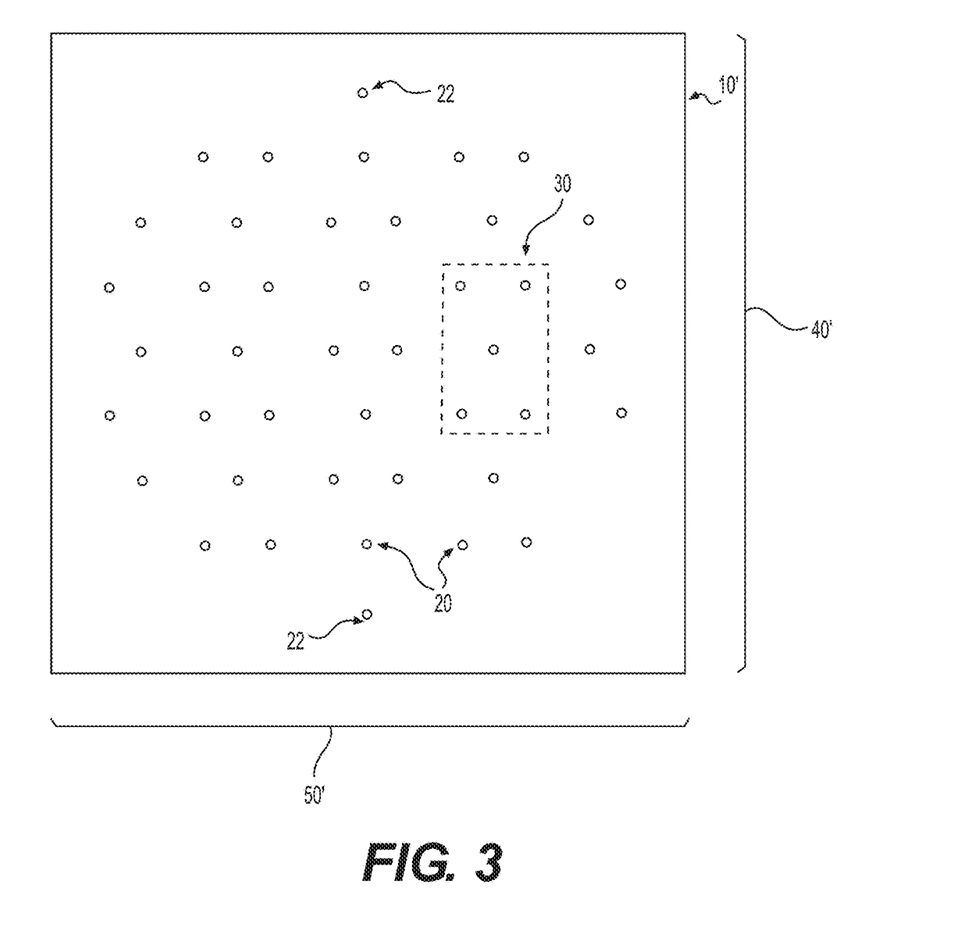
FIG. 3 illustrates a tissue matrix product including holes or perforations, according to certain embodiments.
Figure 4:
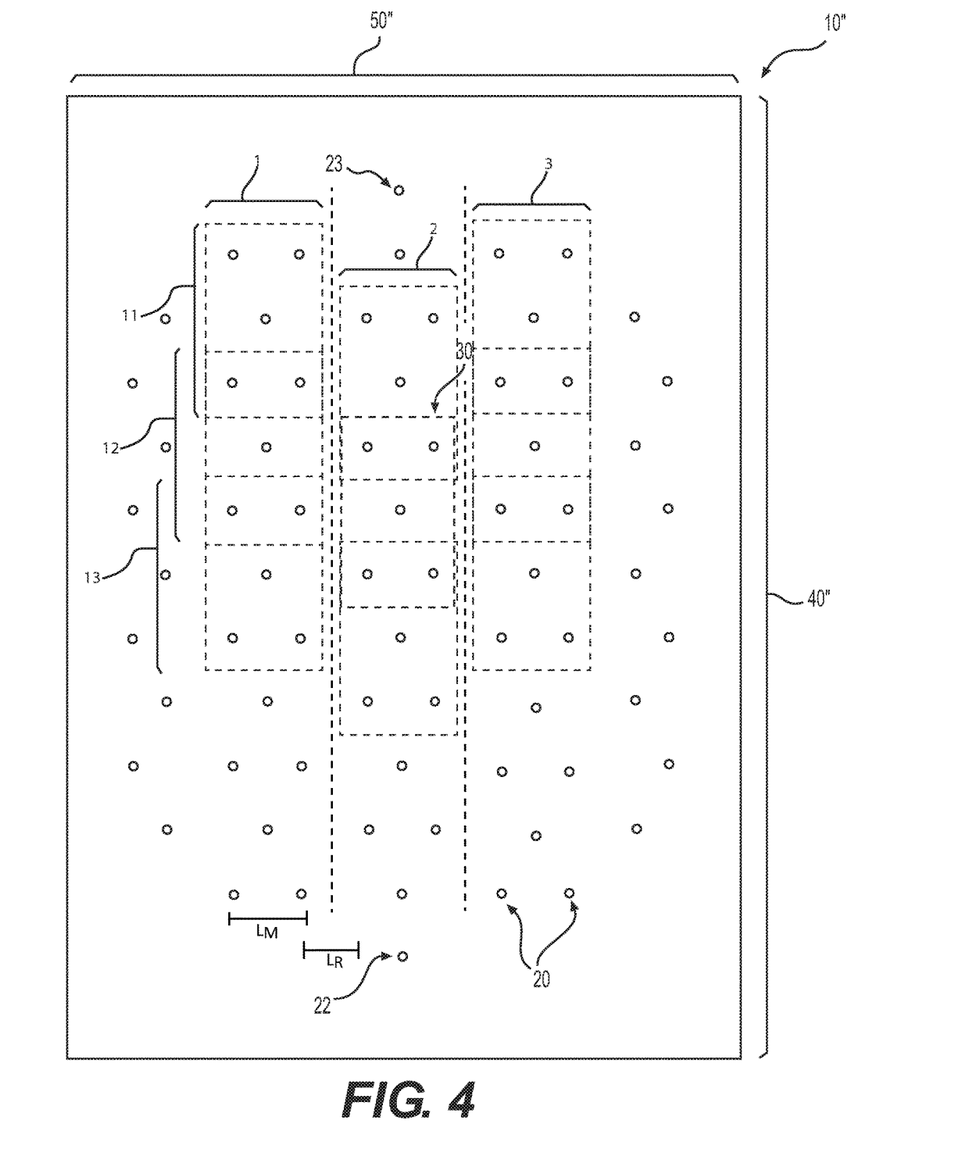
FIG. 4 illustrates a tissue matrix product including holes or perforations, according to certain embodiments.
Figure 5:
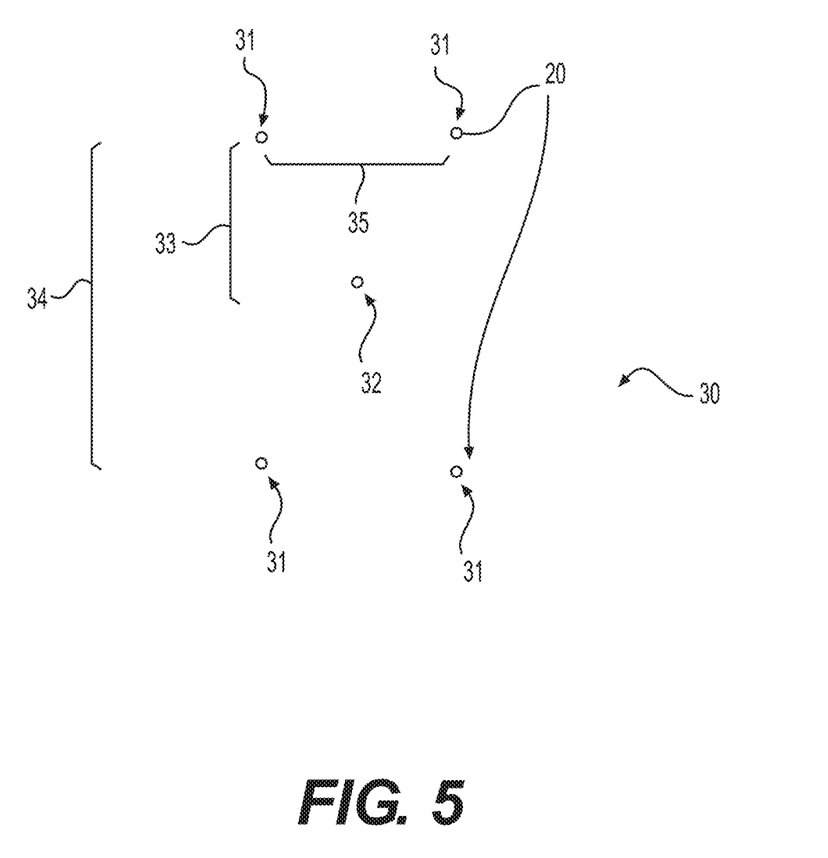
FIG. 5 illustrates a motif for use in creating a hole or perforation pattern, according to certain embodiments.

A suitable motif 30 is illustrated in FIGS. 2B, 3, 4, and 5. As shown, the motif 30 can include five holes 20. In one embodiment the motif 30 has a rectangular shape with a hole 31 positioned at each corner of the rectangle and one hole 32 positioned at the center of the rectangle. Further, as illustrated in FIG. 5, the rectangular shape can have a range of suitable sizes, including a width 35 and a length 34 (the length being double the distance 33 measured along an edge of the rectangle from a corner hole 31 to the center hole 32). In various embodiment the width can be between about 2 and 4 cm, or between about 2.5 and 3.5 cm; the length between about 3 and 5 cm, between about 3.5 and 4.5 cm; and the distance 33 between about 1.5 and 2.5 cm. In one embodiment, the width is about 3 cm and the length 34 about 4 cm, but the width and length can be varied (e.g., scaled at the same ratio or otherwise varied in accordance with the goals described herein).

The motif 30 can be distributed across the sheet of tissue matrix 10 in a variety of patterns. For example, as shown, the motif 30 may be arranged in multiple columns 1, 2, 3, and in rows 11, 12, and, 13. The number of columns 1, 2, 3, and rows may be varied based on the size of the product 10 and the specific number of holes 20 desired. For example, the device of FIG. 2B includes three columns, but suitable devices may include between 1 and 10 columns, or any specific number in between. In addition, each column or row need not include all five holes of a motif. For example, as shown in FIG. 2B, the motifs at some positions, e.g., column 1, rows 11 and 13, have four holes of the motif 30, and the motif at the top and bottom of column 2 have only three holes (holes 23 and 22 are not part of the motif 30 and are discussed below).

The distances between each column 1, 2, 3, and rows 11, 12, 13 can be selected to produce desired hole spacing. For example, in one embodiment, the distance between two columns and the size of the motifs 30 are selected to provide a spacing pattern that reduces linear alignment of holes 20 along various directions of the sheet. In so doing, the mechanical strength of the products 10 is maintained.

Of note, as shown in FIG. 2B, the distance between holes of two columns (Lr) differs from the distance (Lm) between the holes 31 at bottom corners of a motif 30. This variation in distance cause the motifs 30 of two different columns 1, 2 to fall out of alignment, so that the motif is not simply repeated, and the alignment of holes is reduced along oblique axes (81, 83—FIG. 2C).

The products 10 described herein can have a variety of shapes and sizes. For example, each of the flexible sheets of tissue matrix illustrated in FIGS. 2A-2C, 3, and 4 are rectangular, which provides a simple shape for use in abdominal wall procedures. Furthermore, a rectangular shape can be trimmed or reshaped based on a specific patient's needs or surgeon's preferences. It will be appreciated, however, that other shapes can be used including circular, oval, square, triangular, bi-convex, or asymmetric shapes.

The size and shape of each of the holes 20 can also be varied. Generally, however, the holes 20 are sized and shaped to preserve the mechanical properties of the sheet of tissue matrix 10, while allowing fluid flow or passage of sutures or other anchors through the holes. For example, the holes can be sized such that they have a maximum dimension between about 1.5 mm and 2.5 mm, between about 1.6 and 2.4 mm, between 1.7 and 2.3 mm, between 1.8 and 2.2, between 1.9 and 2.1 mm, about 2 mm, or any values within the aforementioned ranges.

Further, the holes 20 can be shaped to maintain sheet mechanical properties. For example, to prevent excess force due to tensile forces of sutures passed through a hole 20 or high stress points from stretching, each hole can have a rounded border (e.g., oval, circular, rounded but asymmetric). In one embodiment, all holes 20 are circular and have a diameter between about 1.5 mm and 2.5 mm, between about 1.6 and 2.4 mm, between 1.7 and 2.3 mm, between 1.8 and 2.2. mm, between 1.9 and 2.1 mm, about 2 mm, or any values within the aforementioned ranges.

In some cases, the size of the holes, position of holes, and other mechanical properties of the tissue matrix 10 are selected to maintain a uniaxial tensile strength of the tissue matrix 10. For example, the product can be configured such that a uniaxial tensile strength (as measured along an axis parallel to the length of the tissue matrix 10) is at least 50%, at least 60%, at least 70%, at least 80%, at least 85%, or at least 90%, or any values in between versus the uniaxial tensile strength of a sheet not having the holes 20.

The hole size and shape as well as other sheet properties (e.g., thickness) can be configured to provide holes that will maintain suture retention strength if sutures or other fixation devices are passed through a hole. For example, the suture retention strength of each hole 20 can be configured such that it is at least 60%, at least 70%, at least 80%, at least 90%, at least 95%, at least 99% or approximately 100% of the suture retention strength of a region of the same tissue matrix without a hole 20.

Suture retention can be measured using a simple technique. Specifically, a suture or suture analog (e.g., a steel wire) can be passed through the tissue to form a loop, and tension can be applied until the material tears. The amount of force (Newtons) needed to tear the tissue is the suture retention strength. The suture retention strength can be measured by passing the suture through one of the holes 20 to measure the suture retention when a hole is used.

In various embodiments, the holes 20 are positioned to minimize or control the number of holes that are linearly aligned along various directions. For example, in certain embodiments, the holes 20 are positioned such that the number of holes that are linearly aligned along an oblique axis 81, 83 of the flexible sheet 10 is kept below a certain value.

As used herein "oblique axis" will be understood to refer to a direction along the flexible sheet that is parallel to the flat top or bottom surfaces of the sheet (when the flexible sheet is laid on a flat surface) but is not parallel to an axis 90 directed along the length 40 or an axis 91 directed along the width 50 of the flexible sheet 10.

In some embodiments, the number of holes that can be linearly aligned along an oblique axis is two or fewer, three or fewer, four or fewer, or five or fewer.

In addition to the holes 20 being provided in a specified pattern, one or more additional holes 22, 23 can be included. For example, as shown in FIG. 2B, one hole 22 is located at a bottom 25 of the sheet, and another hole 23 is located at a top 24 of the sheet. The holes 22, 23 are provided to identify for a surgeon where the top 24 and bottom 25 of the sheet are located (i.e., identify the orientation of the sheet so that the surgeon recognizes how the sheet should be aligned when implanted in an abdominal wall). In particular, using the pattern set forth in FIGS. 2A-2C, the sheet 10 should be implanted such that the holes 22, 23 are generally aligned with an anatomic axis in an superior-inferior (rostral-caudal) direction. It will be appreciated, however, that the holes could be moved to identify a different anatomic direction for different surgical indications.

FIGS. 2A-2B illustrate one embodiment for a flexible sheet of tissue matrix 10 with holes 20. The sheets 10 illustrated therein, however, may be modified in other ways. For example, FIGS. 3 and 4 illustrate tissue matrix products 10', 10" including holes or perforations, but having differing sizes and differing numbers of holes. It should be understood that the size of the products and number of holes may be adjusted based on the size of the patient, the condition to be treated, or other factors determined by a surgeon.

The specific number of holes 20 in the devices 10, 10', 10" illustrated can be varied. For example, a sheet can include between 10 and 80 holes passing through the tissue matrix, between 20 and 40 holes, between 20 and 50 holes, between 10 and 30 holes, between 14 and 64 holes, or other values in between. Further the sheets can be rectangular and have a width between 10 cm and 30 cm, between 10 cm and 25 cm, between 20 cm and 25 cm, or any ranges in between. In addition the devices 10, 10', 10" can have a length between 10 cm and 30 cm, between 15 cm and 30 cm, or between 20 cm and 25 cm.

The products described herein are generally described with reference to acellular tissue matrices, but it will be appreciated that the tissue matrices can be pre-treated with exogenous cells or other therapeutic components prior to or after implantation. Accordingly, the devices can include tissue matrix products from which substantially all native cellular material has been removed, but which include exogenous cellular sources such as stem cells, fibroblasts, platelets, blood cells, or other cell sources.

The devices described herein can be used in a variety of different surgical operations, including in operations for treatment of abdominal wall issues. For example, FIG. 1 illustrates implantation of devices 10 at a variety of different positions within an abdominal wall. Although one of skill in the art will recognize that a certain procedure may require only one of the devices 10 of FIG. 1, each of the illustrated implantation locations (as well as others) may be desirable, depending upon the specific procedure being performed. The illustrated implantation locations would be recognized by surgeons and can include onlay 170, inlay 171, retromuscular 172, preperitoneal 173, or intraperitoneal 174, but additional sites can be used.

In some embodiments, the device 10 may also be implanted next to a drainage device 200, such as a drainage bulb, which may include a tube that passes to a surgical location 220 near an implanted device.

Furthermore, the devices 10 can be implanted during open, laparoscopic, or using any suitable surgical approach. The holes 20 can be used to receive sutures, clips, staples, or other fixation devices that facilitate positioning and securing the device and/or surrounding tissues in place.

The holes 20 can be formed in a variety of ways. For example, in one embodiment, the holes are produced using a machine press with a cutting die selected to include elongated sharpened extensions. The sharpened extensions can be placed in a desired pattern to cut or puncture holes 20 while also including a knife or cutting die to cut the perimeter of the device 10. Alternatively the holes can be cut individually, by hand or using suitable cutting tools.

What is claimed is:

1. A tissue matrix product, comprising:
a flexible sheet comprising a tissue matrix, wherein the flexible sheet includes a group of holes passing through the tissue matrix, wherein the holes are formed in a pattern comprising a motif of five holes having a rectangular shape with a width and a length such that the length is greater than the width, the motif repeating in at least two columns, wherein adjacent columns are spaced apart from one another by a distance different from the width, wherein the distance defines an area without holes.

2. The product of claim 1, wherein the rectangular shape includes a hole positioned at each corner of the rectangular shape and one hole positioned at a center of the rectangular shape.

3. The product of claim 1, wherein the flexible sheet has a rectangular shape.

4. The product of claim 1, wherein the motif is repeated in at least three columns.

5. The product of claim 1, wherein the motif is repeated in at least two rows.

6. The product of claim 5, wherein the motif is repeated in at least three rows.

7. The product of claim 5, wherein a distance between each column is greater than a distance between each row.

8. The product of claim 1, wherein each hole has a maximum dimension between about 1.5 mm and 2.5 mm.

9. The product of claim 1, wherein each hole has a rounded border.

10. The product of claim 1, wherein each hole is circular.

11. The product of claim 1, wherein the tissue matrix comprises an acellular tissue matrix.

12. The product of claim 1, wherein the tissue matrix comprises a dermal tissue matrix.

13. The product of claim 1, wherein the tissue matrix is a human tissue matrix.

14. The product of claim 1, wherein the tissue matrix is a porcine tissue matrix.

15. The product of claim 1, wherein substantially all native cellular material has been removed from the tissue matrix.

16. The product of claim 1, wherein the flexible sheet of tissue matrix with a group of holes has a uniaxial tensile strength measured in any direction along the sheet that is at least 60% of the uniaxial tensile strength of a sheet without the group of holes.

17. The product of claim 16, wherein the suture retention strength of any hole of the group of holes is at least 80% of the suture retention strength of a region of the tissue matrix without the hole.

18. The tissue matrix product of claim 1, wherein the motif of five holes in a first column of the two columns is not laterally aligned with the motif of five holes in a second column of the two columns.

* * * * *